(12) United States Patent
Giampietro et al.

(10) Patent No.: US 9,376,401 B2
(45) Date of Patent: *Jun. 28, 2016

(54) PREPARATION OF 1,3-(SUBSTITUTED-DIARYL)-1,2,4-TRIAZOLES AND INTERMEDIATES THEREFROM

(71) Applicant: Dow AgroSciences LLC, Indianapolis, IN (US)

(72) Inventors: Natalie C. Giampietro, Carmel, IN (US); Gary D. Crouse, Noblesville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 11 days.

This patent is subject to a terminal disclaimer.

(21) Appl. No.: 14/192,405

(22) Filed: Feb. 27, 2014

(65) Prior Publication Data

US 2014/0275556 A1    Sep. 18, 2014

Related U.S. Application Data

(60) Provisional application No. 61/778,480, filed on Mar. 13, 2013.

(51) Int. Cl.
*C07D 249/08* (2006.01)

(52) U.S. Cl.
CPC .................................. *C07D 249/08* (2013.01)

(58) Field of Classification Search
None
See application file for complete search history.

(56) References Cited

U.S. PATENT DOCUMENTS

| | | | |
|---|---|---|---|
| 2008/0280869 A1* | 11/2008 | Almstead et al. | 514/210.02 |
| 2012/0053216 A1 | 3/2012 | Creemer et al. | |
| 2013/0019348 A1 | 1/2013 | Crouse et al. | |

FOREIGN PATENT DOCUMENTS

WO    WO2011/017513    2/2011

OTHER PUBLICATIONS

PCT International Search Report/Written Opinion for PCT/US2014/019000, completed May 6, 2014.

* cited by examiner

*Primary Examiner* — Alicia L Otton
(74) *Attorney, Agent, or Firm* — Yung H. Lee; Barnes & Thornburg LLP

(57) ABSTRACT

The invention in this document is related to the field of preparation of 1,3-(substituted-diaryl)-1,2,4-triazoles and certain intermediates derived therefrom, where said intermediates are useful in the preparation of certain pesticides disclosed in U.S. Pat. No. 8,178,658.

9 Claims, No Drawings

PREPARATION OF 1,3-(SUBSTITUTED-DIARYL)-1,2,4-TRIAZOLES AND INTERMEDIATES THEREFROM

CROSS REFERENCE TO RELATED APPLICATIONS

This application claims the benefit of U.S. Provisional Patent Application Ser. No. 61/778,480 filed Mar. 13, 2013, the entire disclosure of which is hereby expressly incorporated by reference.

FIELD OF THE DISCLOSURE

This document is related to the field of preparation of 1,3-(substituted-diaryl)-1,2,4-triazoles and certain intermediates derived therefrom, where said intermediates are useful in the preparation of certain pesticides.

BACKGROUND OF THE DISCLOSURE

U.S. Pat. No. 8,178,658 discloses pesticidal compositions comprising a compound having the following structure:

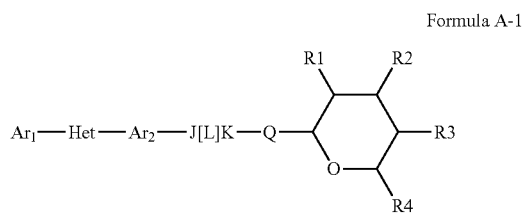

Formula A-1 wherein $Ar_1$, Het, $Ar_2$, J, L, K, Q, R1, R2, R3, and R4 are disclosed in the patent. While processes are disclosed on how to make such compounds, and such processes are useful, it is desired to have more useful processes to make these compounds. In particular, it is desirable to have more commercially useful routes (particularly those with fewer process steps) to certain substituted triaryl intermediates disclosed in the patent that are useful in producing the compounds of Formula A-1.

DETAILED DESCRIPTION OF THE DISCLOSURE

Throughout this document, all temperatures are given in degrees Celsius, and all percentages are weight percentages unless otherwise stated.

The term "alkyl", as well as derivative terms such as "haloalkyl" and "haloalkoxy", as used herein, include within their scope straight chain, branched chain and cyclic moieties. Thus, typical alkyl groups are methyl, ethyl, propyl, butyl, pentyl, hexyl, 1-methylethyl, 1,1-dimethylethyl, 1-methylpropyl, 2-methylpropyl, cyclopropyl, cyclobutyl, cyclopentyl and cyclohexyl. The term "alkenyl", as used herein, means an acyclic, unsaturated (at least one carbon-carbon double bond), branched or unbranched substituent consisting of carbon and hydrogen, for example, vinyl, allyl, butenyl, pentenyl or hexenyl. The term "alkynyl", as used herein, means an acyclic, unsaturated (at least one carbon-carbon triple bond), branched or unbranched substituent consisting of carbon and hydrogen, for example, ethynyl, propargyl, butynyl, pentynyl or hexynyl. The terms "haloalkyl" and "haloalkoxy" includes alkyl or alkoxy groups substituted with from one to the maximum possible number of halogen atoms, all combinations of halogens included. The term "halogen" or "halo" includes fluorine, chlorine, bromine and iodine, with fluorine being preferred.

In Scheme 1, diphenyl triazoles of Formula 1.4, wherein $R_1$ is $C_1$-$C_6$ haloalkoxy, preferably trifluoromethoxy and pentafluoroethoxy, can be prepared as outlined therein.

The intermediates of formula 1.2, wherein X is Cl, Br, or I, can be prepared by reacting 3-(bromo, chloro, or iodo)-1H-1,2,4-triazole (a molecule of formula 1.1) (Kroeger, C. F.; Miethchen, R., Chemische Berichte (1967), 100(7), 2250) with a 4-($C_1$-$C_6$)haloalkoxy-1-halobenzene (wherein each halo is independently I, Br, Cl, or F), in the presence of a metal catalyst such as copper (I) iodide (CuI), copper (I) oxide ($Cu_2O$), or mixtures thereof, and a base, for example, cesium carbonate ($Cs_2CO_3$), potassium phosphate ($K_3PO_4$), potassium carbonate ($K_2CO_3$), or mixtures thereof, with or without a ligand, for example, quinolin-8-ol or N,N'-dimethyl ethylenediamine or other 1,2-diamines or glycine, in a polar aprotic solvent, for example, acetonitrile (MeCN), dimethylformamide (DMF), dimethyl sulfoxide (DMSO), or mixtures thereof. This reaction can be conducted at temperatures from about 70° C. to about 150° C.

Compounds of formula 1.3, wherein $R_2$ is H or ($C_1$-$C_6$) alkyl preferably methyl or ethyl, can be prepared from compounds of formula 1.2, by reacting with ($R_2$—OC(=O)-phenyl)boronic acid, or ($R_2$—OC(=O)-phenyl)boronic ester, or a potassium $R_2$—OC(=O)-phenyl) trifluoroborate salt, for example, 4-carboxyphenylboronic acid, (4-(methoxycarbonyl)phenyl)boronic acid, (4-(ethoxycarbonyl)phenyl)boronic acid. The reaction is conducted in the presence of a base, for example, $K_2CO_3$, sodium carbonate ($Na_2CO_3$), sodium bicarbonate ($NaHCO_3$), potassium fluoride (KF), or mixtures thereof. Furthermore, the reaction is conducted in the presence of a palladium catalyst, for example, bis(triphenylphosphine)palladium (II) chloride ($PdCl_2(PPh_3)_2$) or tetrakis(triphenylphosphine)palladium (0) ($Pd(PPh_3)_4$). Optionally, a ligand can be present. The reaction is conducted in a polar aprotic solvent, for example, MeCN, dioxane, dimethoxyethane (DME), tetrahydrofuran (THF), or mixtures thereof, and water. The reaction is conducted at a temperature from about 80° C. and about 150° C. The reaction can be heated using traditional methods or microwave heating. The reaction is conducted at a pressure from about 0 KPa to about 3000 kPa. Generally, the molar ratio of the compounds of formula 1.2 to the ($R_2$—OC(=O)-phenyl)boronic acid, ($R_2$—OC(=O)-phenyl)boronic ester, or potassium $R_2$—OC(=O)-phenyl) trifluoroborate salt is about 1 equivalent of the compound of formula 1.2 to about 0.5-2 equivalents of the boronic acid, boronic ester, or borate salt, preferably, from about 1 equivalent of a compound of formula 1.2 to about 1-1.5 equivalents of the boronic acid, boronic ester, or borate salt, and even more preferably about from about 1 equivalent of the compound of formula 1.2 to about 1-1.1 equivalents of the boronic acid, boronic ester, or borate salt.

Compounds of formula 1.3 can be then saponified to produce the compounds of formula 1.4. This reaction can be conducted in a polar protic solvent, for example, methanol (MeOH), ethanol (EtOH), n-butanol, isopropanol, or mixtures thereof, or in a polar aprotic solvent, for example, THF. The reaction is conducted in the presence of an alkali hydroxide base, for example, sodium (NaOH), potassium (KOH), or lithium hydroxide (LiOH), and water. The reaction can be conducted at a temperature from about 20° C. to about 60° C., and preferably from about 20° C. to about 30° C. The pH of the reaction mixture is from about 8 to about 14, and preferably from about 10 to about 12.

Scheme 1

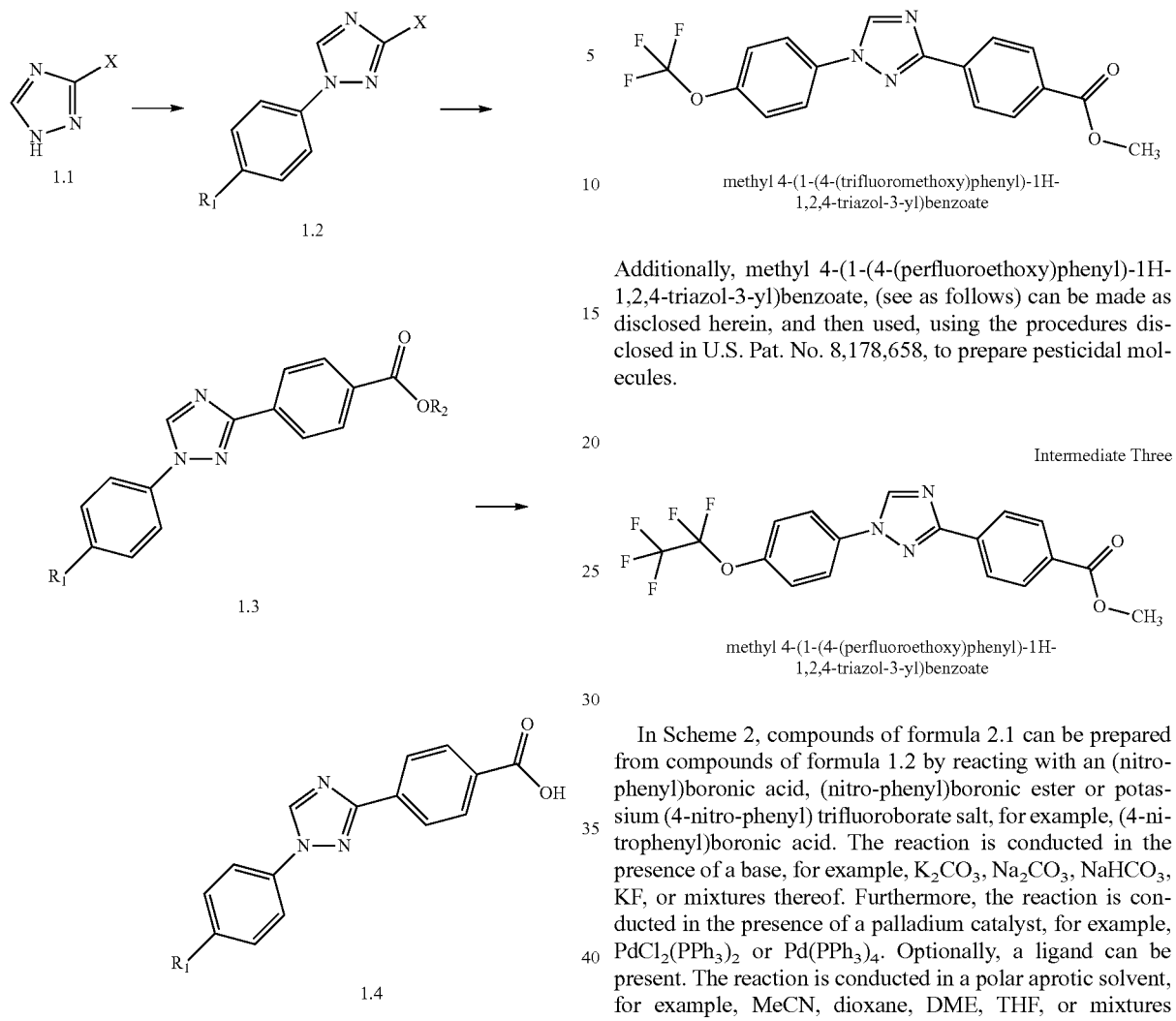

Compounds of formula 1.4 can be used as intermediates to form pesticides as disclosed in U.S. Pat. No. 8,178,658. For example, 4-(1-(4-(trifluoromethoxy)phenyl)-1H-1,2,4-triazol-3-yl)benzoic acid, (see as follows) can be made as disclosed herein, and then used, using the procedures disclosed in U.S. Pat. No. 8,178,658, to prepare pesticidal molecules.

Intermediate One

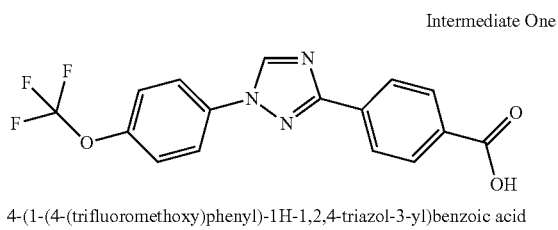 [SMILES: O=C(O)c1ccc(-c2ncn(-c3ccc(OC(F)(F)F)cc3)n2)cc1]

4-(1-(4-(trifluoromethoxy)phenyl)-1H-1,2,4-triazol-3-yl)benzoic acid

Additionally, methyl 4-(1-(4-(trifluoromethoxy)phenyl)-1H-1,2,4-triazol-3-yl)benzoate, (see as follows) can be made as disclosed herein, and then used, using the procedures disclosed in U.S. Pat. No. 8,178,658, to prepare pesticidal molecules.

Intermediate Two methyl 4-(1-(4-(trifluoromethoxy)phenyl)-1H-1,2,4-triazol-3-yl)benzoate Additionally, methyl 4-(1-(4-(perfluoroethoxy)phenyl)-1H-1,2,4-triazol-3-yl)benzoate, (see as follows) can be made as disclosed herein, and then used, using the procedures disclosed in U.S. Pat. No. 8,178,658, to prepare pesticidal molecules.

Intermediate Three methyl 4-(1-(4-(perfluoroethoxy)phenyl)-1H-1,2,4-triazol-3-yl)benzoate In Scheme 2, compounds of formula 2.1 can be prepared from compounds of formula 1.2 by reacting with an (nitro-phenyl)boronic acid, (nitro-phenyl)boronic ester or potassium (4-nitro-phenyl) trifluoroborate salt, for example, (4-nitrophenyl)boronic acid. The reaction is conducted in the presence of a base, for example, $K_2CO_3$, $Na_2CO_3$, $NaHCO_3$, KF, or mixtures thereof. Furthermore, the reaction is conducted in the presence of a palladium catalyst, for example, $PdCl_2(PPh_3)_2$ or $Pd(PPh_3)_4$. Optionally, a ligand can be present. The reaction is conducted in a polar aprotic solvent, for example, MeCN, dioxane, DME, THF, or mixtures thereof. The reaction is conducted at a temperature from about 80° C. and about 150° C. The reaction can be heated using traditional methods or microwave heating. The reaction is conducted at a pressure from about 0 KPa to about 3000 kPa. Generally, the molar ratio of the compounds of formula 1.2 to the (nitro-phenyl)boronic acid, (nitro-phenyl)boronic ester, or borate salt is about 1 equivalent of the compound of formula 1.2 to about 0.5-2 equivalents of the boronic acid, boronic ester, or trifluoroborate salt, preferably, from about 1 equivalent of a compound of formula 1.2 to about 1-1.5 equivalents of the boronic acid, boronic ester, or borate salt, and even more preferably about from about 1 equivalent of the compound of formula 1.2 to about 1-1.1 equivalents of the boronic acid, boronic ester, or borate salt.

Compounds of formula 2.1 can be reduced to produce compounds of formula 2.2 using methods disclosed in U.S. Pat. No. 8,178,658. Furthermore, this reaction can be carried out in a wide variety of organic solvents including, for example, polar protic solvents, for example, MeOH, EtOH, n-butanol, isopropanol, or mixtures thereof, and polar aprotic solvents, for example, THF and ethyl acetate (EtOAc), or organic acids, for example, acetic acid (AcOH). The reduction is conducted in the presence of a palladium catalyst, for example, palladium on carbon (Pd/C), and in the presence of a hydrogen source, for example hydrogen gas, ammonium salts, for example, ammonium formate, and cyclohexadiene. The reaction can be conducted at a temperature from about 20° C. to about 50° C., and preferably from about 20° C. to about 30° C. When hydrogen gas is used, the reaction can be conducted at a pressure from about 100 kPa to about 700 kPa and preferably from about 100 kPa to about 350 kPa. See also WO 2009/102736 A1.

Compounds of formula 2.2 can be used as intermediates to form pesticides as disclosed in U.S. Pat. No. 8,178,658.

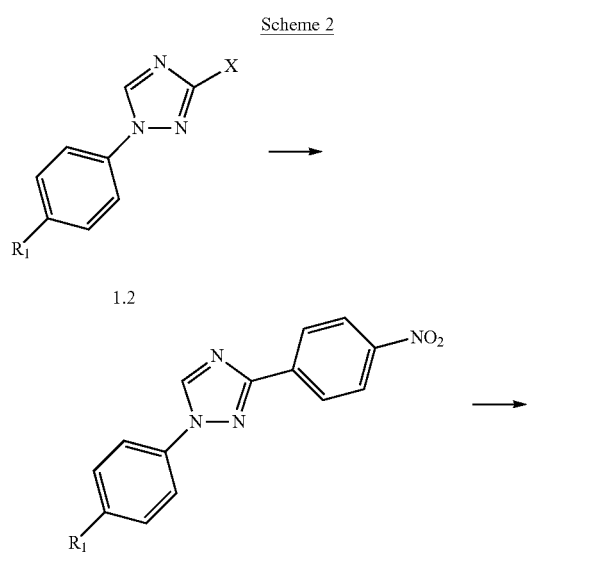

Scheme 2

1.2

2.1

2.2

In Scheme 3, compounds of formula 3.1, where $R_3$ is hydrogen and $R_4$ is a amine protecting group ("APG") such as tert-butyloxycarbonyl ("Boc") or a benzyl carbamate ("CBZ"), can be prepared from compounds of formula 1.2, by reacting with an (APG-NH-phenyl)boronic acid, (APG-NH-phenyl)boronic ester, or a potassium (APG-NH-phenyl) trifluoroborate salt, such as tert-butyl (4-(4,4,5,5-tetramethyl-1,3,2-dioxaborolan-2-yl)phenyl)carbamate. The reaction is conducted in the presence of a base, for example, $K_2CO_3$, $Na_2CO_3$, $NaHCO_3$, KF, or mixtures thereof. Furthermore, the reaction is conducted in the presence of a palladium catalyst, for example, $PdCl_2(PPh_3)_2$ or $Pd(PPh_3)_4$. Optionally, a ligand can be present. The reaction is conducted in a polar aprotic solvent, for example, MeCN, dioxane, DME, THF, or mixtures thereof. The reaction is conducted at a temperature from about 80° C. and about 150° C. The reaction can be heated using traditional methods or microwave heating. The reaction is conducted at a pressure from about 0 KPa to about 3000 kPa. Generally, the molar ratio of the compounds of formula 1.2 to the (APG-NH-phenyl)boronic acid, (APG-NH-phenyl) boronic ester, or potassium (APG-NH-phenyl) trifluoroborate salt, is about 1 equivalent of the compound of formula 1.2 to about 0.5-2 equivalents of the boronic acid, boronic ester, borate salt, preferably, from about 1 equivalent of a compound of formula 1.2 to about 1-1.5 equivalents of the boronic acid, boronic ester or borate salt, and even more preferably about from about 1 equivalent of the compound of formula 1.2 to about 1-1.1 equivalents of the boronic acid, boronic ester, borate salt.

Compounds of formula 2.2, can be prepared from compounds of formula 3.1, wherein APG is a Boc group, by reaction with an acid such as trifluoroacetic acid (TFA) in a solvent. Typically, organic and inorganic acids can be used, and typically the reaction usually involves an acid (for example, HCl, TFA), but any one of a number of possible Boc group cleavage conditions are applicable in this case. TFA conditions are most typical for this transformation (See Greene, T. W. Greene's Protective Groups in Organic Synthesis, 2007, pp. 725-735). Furthermore, a wide range of solvents may be used in this reaction, ranging from dichloromethane ($CH_2Cl_2$), MeOH, toluene, dioxane, THF, or mixtures thereof.

Compounds of formula 2.2 can be prepared from compounds of formula 3.1 wherein $R_4$ is a CBZ group by means of catalytic reduction (hydrogen gas and a catalyst such as Pd/C). Other examples of useful amine protecting groups may be found in the above monograph, and are well known to those skilled in the art.

Compounds of formula 2.2 can be used as intermediates to form pesticides as disclosed in U.S. Pat. No. 8,178,658.

Scheme 3

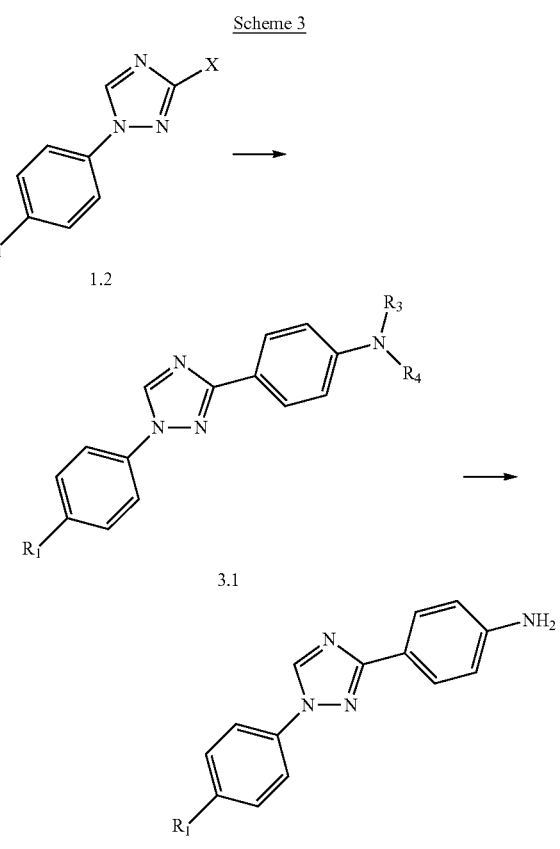

1.2

3.1

2.2

In Scheme 4, compounds of formula 2.2 can be prepared from compounds of formula 1.2, by reacting with an ($H_2N$- phenyl)boronic acid or (H$_2$N-phenyl)boronic ester or a potassium (H$_2$N-phenyl) trifluoroborate salt, such as 4-(4,4,5,5-tetramethyl-1,3,2-dioxaborolan-2-yl)aniline. The reaction is conducted in the presence of a base, for example, K$_2$CO$_3$, Na$_2$CO$_3$, NaHCO$_3$, KF, or mixtures thereof. Furthermore, the reaction is conducted in the presence of a palladium catalyst, for example, PdCl$_2$(PPh$_3$)$_2$ or Pd(PPh$_3$)$_4$. Optionally, a ligand can be present. The reaction is conducted in a polar aprotic solvent such as MeCN, dioxane, DME, THF, or mixtures thereof. The reaction is conducted at a temperature from about 80° C. and about 150° C. The reaction can be heated using traditional methods or microwave heating. The reaction is conducted at a pressure from about 0 KPa to about 3000 kPa. Generally, the molar ratio of the compounds of formula 1.2 to the ((H$_2$N-phenyl)boronic acid, (H$_2$N-phenyl)boronic ester, or potassium (H$_2$N-phenyl) trifluoroborate salt, is about 1 equivalent of the compound of formula 1.2 to about 0.5-2 equivalents of the boronic acid, boronic ester, borate salt, preferably, from about 1 equivalent of a compound of formula 1.2 to about 1-1.5 equivalents of the boronic acid. boronic ester borate salt, and even more preferably about from about 1 equivalent of the compound of formula 1.2 to about 1-1.1 equivalents of the boronic acid, boronic ester, or borate salt.

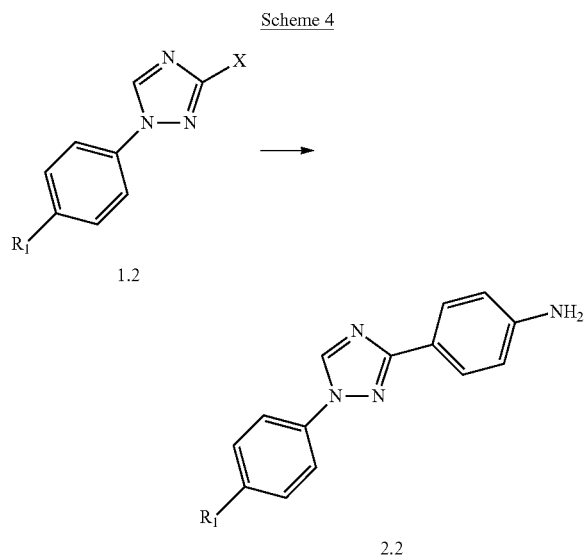

Compounds of formula 2.2 can be used as intermediates to form pesticides as disclosed in U.S. Pat. No. 8,178,658.

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1

Preparation of 3-bromo-1-(4-(trifluoromethoxy)phenyl)-1H-1,2,4-triazole (Compound 1)

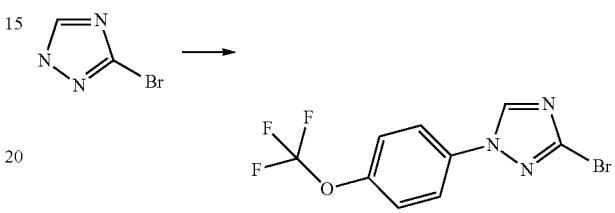

To a 250 mL reaction flask was added 3-bromo-1H-1,2,4-triazole (5 g, 33.8 mmol), CuI (0.644 g, 3.38 mmol) and Cs$_2$CO$_3$ (11.01 g, 33.8 mmol). The flask was evacuated/backfilled with nitrogen gas, and then DMSO (33.8 ml) and 1-iodo-4-(trifluoromethoxy)benzene (4.87 g, 16.90 mmol) were added. The reaction mixture was heated to 100° C. for 20 hours (h). The reaction wascooled to room temperature (RT), diluted with EtOAc and filtered through a plug of Celite®. The Celite® was further washed with EtOAc. Water was added to the combined organics, and the layers were separated. The aqueous phase was neutralized to pH 7, and further extracted with EtOAc. The combined organics were concentrated in vacuo. Purification via flash column chromatography using EtOAc/hexanes as eluent provided the title compound as an off-white solid (3.78 g, 73%): mp 69-70° C.; $^1$H NMR (400 MHz, CDCl$_3$) δ 8.44 (s, 1H), 7.70 (d, J=8.9 Hz, 2H), 7.38 (d, J=8.5 Hz, 2H); $^{19}$F NMR (376 MHz, CDCl$_3$) δ-58.04; EIMS m/z 307 ([M]$^{+).}$ Example 2

Preparation of methyl 4-(1-(4-(trifluoromethoxy)phenyl)-1H-1,2,4-triazol-3-yl)benzoate (Compound 2)

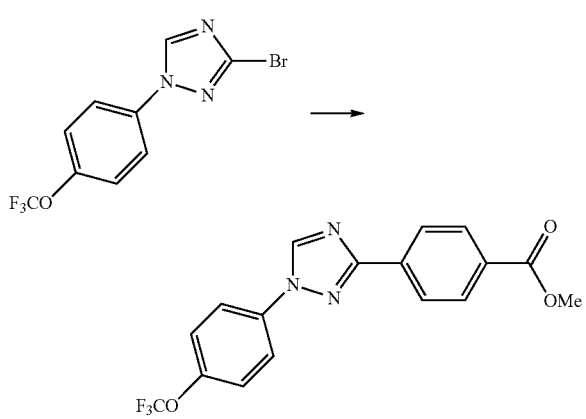

A microwave vial was charged with (4-(methoxycarbonyl)phenyl)boronic acid (70.1 mg, 0.390 mmol), 3-bromo-1-(4-(trifluoromethoxy)phenyl)-1H-1,2,4-triazole (100 mg, 0.325 mmol), aqueous Na$_2$CO$_3$ (1 M, 1.298 mL, 1.298 mmol), and Pd(PPh$_3$)$_4$ (37.5 mg, 0.032 mmol). The reaction vial was capped and evacuated/backfilled with nitrogen gas (3×). DME (2 mL) was added, the vial was capped, heated at 100° C. for 15 minutes (min) in a Biotage Initiator® microwave reactor with external IR-sensor temperature monitoring from the side of the vessel. The reaction mixture was cooled to RT, and diluted with CH$_2$Cl$_2$ (3 mL) and water. The organic and aqueous phase was separated with a phase separator, and the organics were concentrated in vacuo. Purification via flash column chromatography using EtOAc/hexanes as eluent yielded the title compound as a white solid (62 mg, 52%): $^1$H NMR (400 MHz, CDCl$_3$) δ 8.60 (s, 1H), 8.28 (m, 2H), 8.15 (m, 2H), 7.81 (m, 2H), 7.41 (m, 2H), 3.96 (s, 3H); $^{19}$F NMR (376 MHz, CDCl$_3$) δ −58.02; ESIMS m/z 364 ([M+H]$^+$).

Example 3

Preparation of methyl 4-(1-(4-(perfluoroethoxy)phenyl)-1H-1,2,4-triazol-3-yl)benzoate (Compound 3)

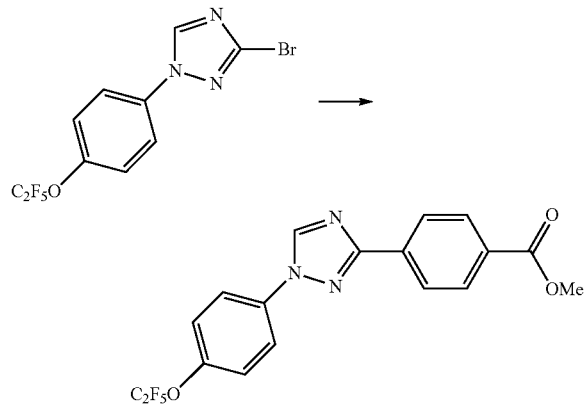

Step 1. 3-Bromo-1-(4-(pentafluoroethoxy)phenyl)-1H-1,2,4-triazole: Conditions described in Example 1 were used to convert 1-iodo-4-pentafluoroethoxybenzene and 3-bromo-1,3,4-triazole into 3-bromo-1-(4-(pentafluoroethoxy)phenyl)-1H-1,2,4-triazole (32%): mp 72-74° C., $^1$H NMR (400 MHz, CDCl$_3$) δ 8.44 (s, 1H), 7.75-7.68 (m, 2H), 7.42-7.36 (m, 2H); $^{19}$F NMR (376 MHz, CDCl$_3$) δ −85.94, −87.92. ESIMS m/z 358 ([M+H])$^+$.

Step 2: A microwave vial was charged with methyl 4-(4,4,5,5-tetramethyl-1,3,2-dioxaborolan-2-yl)benzoate (147 mg, 0.561 mmol), 3-bromo-1-(4-(pentafluoroethoxy)phenyl)-1H-1,2,4-triazole (200 mg, 0.559 mmol), NaHCO$_3$ (94 mg, 1.2 mmol), and Pd(PPh$_3$)$_4$ (39 mg, 0.034 mmol). Dioxane (3.8 mL) and water (1.2 mL) were added, the reaction vial was capped, and the reaction was heated at 140° C. for 30 min in a Biotage Initiator® microwave reactor with external IR-sensor temperature monitoring from the side of the vessel. The reaction mixture was cooled to RT, and allowed to stand overnight. A white solid formed, which was filtered and air-dried to give the title compound as a white solid (146 mg, 62%): mp 192-195° C., $^1$H NMR (400 MHz, CDCl$_3$) δ 8.61 (s, 1H), 8.28 (d, J=9.0 Hz, 2H), 8.19-8.12 (d, J=9.0 Hz, 2H), 7.82 (d, J=9.0 Hz, 2H), 7.45-7.38 (m, 2H), 3.95 (s, 3H); $^{19}$F NMR (376 MHz, CDCl$_3$) δ −85.90, −87.86; ESIMS m/z 414 ([M+H])$^+$.

Example 4

Preparation of 4-(1-(4-(trifluoromethoxy)phenyl)-1H-1,2,4-triazol-3-yl)benzoic acid (Compound 4)

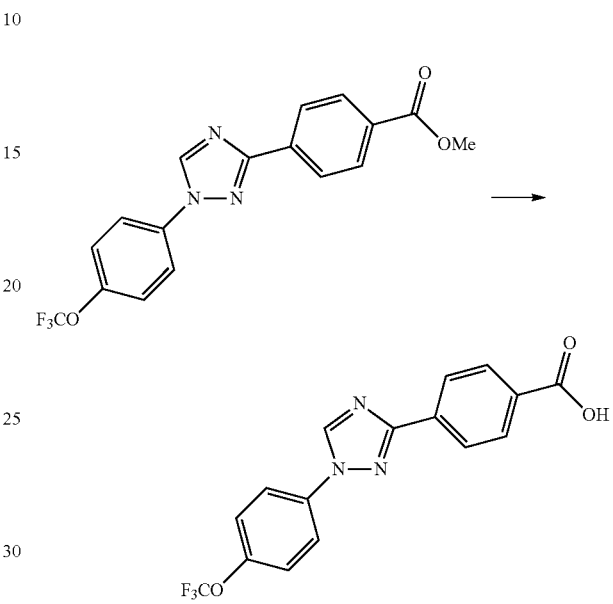

To methyl 4-(1-(4-(trifluoromethoxy)phenyl)-1H-1,2,4-triazol-3-yl)benzoate (0.332 g, 0.914 mmol) in THF (6 mL) and water (3 mL) was added LiOH (0.066 g, 2.74 mmol). The solution immediately turned from yellow to orange-red. The reaction was stirred vigorously at RT for 16 h. The solution was acidified to pH 2 and diluted with water and CH$_2$Cl$_2$. The layers were separated and the aqueous layer was extracted with EtOAc (3×10 mL) and the combined organic fractions were washed with water (10 mL) and brine (10 mL), dried over magnesium sulfate (MgSO$_4$), filtered and concentrated to give the title compound as a tan solid (0.29 g, 91%): mp 228-233° C.; $^1$H NMR (400 MHz, DMSO-d$_6$) δ 10.55-10.24 (m, 1H), 9.46 (s, 1H), 8.23 (d, J=8.0 Hz, 2H), 8.09 (d, J=7.9 Hz, 4H), 7.64 (d, J=8.5 Hz, 2H); ESIMS m/z 350 ([M+H]$^+$).

Example 5

Preparation of 4-(1-(4-(perfluoroethoxy)phenyl)-1H-1,2,4-triazol-3-yl)benzoic acid (Compound 5)

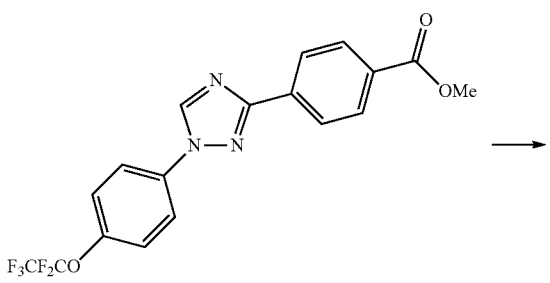

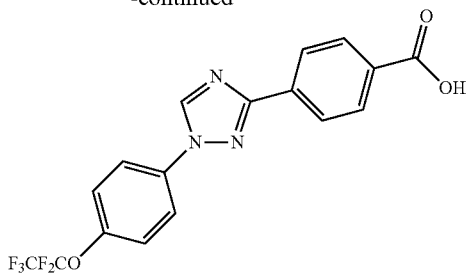

In a 250 mL round bottom flask equipped with an overhead stirrer, thermocouple, and nitrogen inlet was added methyl 4-(1-(4-(perfluoroethoxy)phenyl)-1H-1,2,4-triazol-3-yl)benzoate (11.1 g, 26.9 mmol) and THF (100 mL). To this yellow suspension was added water (10 mL) and lithium hydroxide monohydrate (3.4 g, 81 mmol). There was no change in reaction appearance and temperature (20.5° C.). The reaction was stirred at 23° C. for 39 h during which it became a yellow solution. A heating mantle was attached to the reaction flask and the flask was heated to an internal temperature of 60° C. for 2.5 hrs. The reaction was then cooled to 4° C. in an ice bath and water (100 mL) was added, providing a light yellow solution. Concentrated HCl (8.0 g) was added (note: exothermic) which gave a thick white precipitate. The white suspension was stirred at 5° C. for 30 min and then the solid was collected by vacuum filtration and washed with water (2×25 mL). The white wet cake was allowed to dry in air for 3 h, and was then placed into a vacuum oven (50° C., 700 mm Hg vacuum, 16 h). This gave the title compound as a white solid (10.3 g, 96%): mp 227-229° C.; $^1$H NMR (400 MHz, CDCl$_3$) δ 8.65 (s, 1H), 8.32 (d, J=8.4 Hz, 2H), 8.23 (d, J=8.4 Hz, 2H), 7.84 (d, J=8.9 Hz, 1H), 7.42 (d, J=8.9 Hz, 2H).

Example 6

Preparation of 3-(4-nitrophenyl)-1-(4-(trifluoromethoxy)phenyl)-1H-1,2,4-triazole (Compound 6)

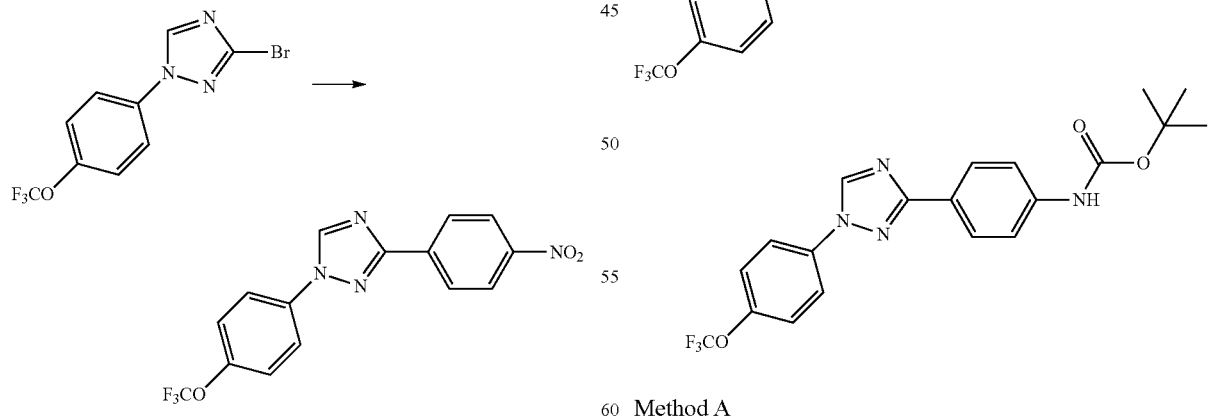

Method A

A microwave vial was charged with (4-nitrophenyl)boronic acid (98 mg, 0.584 mmol), 3-bromo-1-(4-(trifluoromethoxy)phenyl)-1H-1,2,4-triazole (150 mg, 0.487 mmol), Na$_2$CO$_3$ (1 M, 1.948 mL, 1.948 mmol), and Pd(PPh$_3$)$_4$ (56.3 mg, 0.049 mmol). The reaction vial was capped and then evacuated/backfilled with nitrogen gas (3×). DME (2 mL) was added and the reaction was heated at 100° C. for 15 min in a Biotage Initiator® microwave reactor with external IR-sensor temperature monitoring from the side of the vessel. The reaction mixture was cooled to RT, diluted with CH$_2$Cl$_2$, and water was added. The layers were separated with a phase separator. The organics were concentrated and the residue was purified via flash column chromatography using EtOAc/hexanes as eluent to yield the title compound as a yellow solid (82 mg, 47%): mp 146-148 C; $^1$H NMR (400 MHz, CDCl$_3$) δ 8.63 (s, 1H), 8.36 (m, 4H), 7.82 (m, 2H), 7.42 (dq, J=7.9, 1.0 Hz, 2H); $^{19}$F NMR (376 MHz, CDCl$_3$) 5-58.01; ESIMS m/z 351.1 ([M+H]$^+$).

Method B

To a 5-mL microwave vial was added 3-bromo-1-(4-(trifluoromethoxy)phenyl)-1H-1,2,4-triazole (150 mg, 0.487 mmol)), (4-nitrophenyl)boronic acid (98 mg, 0.584 mmol)], KF (73.6 mg, 1.266 mmol)), and PdCl$_2$(PPh$_3$)$_2$ (34.2 mg, 0.049 mmol). Subsequently, MeCN (2.092 mL))/water (2.092 mL)) was added. The reaction vial was then sealed and the reaction was heated at 115° C. for 15 min in a Biotage Initiator® microwave reactor with external IR-sensor temperature monitoring from the side of the vessel. The reaction mixture was cooled to RT, diluted with CH$_2$Cl$_2$ and water. The organics were collected using a phase separator and concentrated. The crude product was purified by flash column chromatography using EtOAc/hexanes to yield the title compound as a yellow solid (65 mg, 38%): $^1$H NMR (400 MHz, CDCl$_3$) δ 8.63 (s, 1H), 8.36 (m, 3H), 7.82 (m, 2H), 7.42 (m, 2H); $^{19}$F NMR (376 MHz, CDCl$_3$) 5-58.01; ESIMS m/z 351.1 ([M+H]$^+$).

Example 7

Preparation of tert-butyl (4-(1-(4-(trifluoromethoxy)phenyl)-1H-1,2,4-triazol-3-yl)phenyl)carbamate (Compound 7)

Method A

A microwave vial was charged with (4-((tert-butoxycarbonyl)amino)phenyl)boronic acid (139 mg, 0.584 mmol), 3-bromo-1-(4-(trifluoromethoxy)phenyl)-1H-1,2,4-triazole (150 mg, 0.487 mmol), Na$_2$CO$_3$ (1 M, 1.948 mL, 1.948 mmol), and Pd(PPh$_3$)$_4$ (56.3 mg, 0.049 mmol). The reaction vial was capped, and evacuated/backfilled with nitrogen gas (3×). DME (2 mL) was added and the reaction was heated at 100° C. for 15 min in a Biotage Initiator® microwave reactor with external IR-sensor temperature monitoring from the side of the vessel. The reaction mixture was cooled to RT, diluted with CH$_2$Cl$_2$, and water was added. The layers were separated with a phase separator. The organic layer was concentrated and then purified via flash column chromatography to yield the title compound as an off white solid (156 mg, 75%): mp 179-181° C.; $^1$H NMR (400 MHz, CDCl$_3$) δ 8.54 (s, 1H), 8.12 (m, 2H), 7.79 (m, 2H), 7.48 (m, 2H), 7.38 (m, 2H), 1.54 (s, 9H); $^{19}$F NMR (376 MHz, CDCl$_3$) 5-58.03; ESIMS m/z 421.3 ([M+H]$^+$).

Method B

To a 5-mL microwave vial was added (4-((tert-butoxycarbonyl)amino)phenyl)boronic acid (139 mg, 0.584 mmol)),3-bromo-1-(4-(trifluoromethoxy)phenyl)-1H-1,2,4-triazole (150 mg, 0.487 mmol)], KF (73.6 mg, 1.266 mmol)), and PdCl$_2$(PPh$_3$)$_2$ (34.2 mg, 0.049 mmol). Subsequently, MeCN (2.092 mL)/water (2.092 mL) was added. The reaction vial was then sealed and the reaction was heated at 115° C. for 20 min in a Biotage Initiator® microwave reactor with external IR-sensor temperature monitoring from the side of the vessel. The reaction mixture was cooled to RT, diluted with CH$_2$Cl$_2$ and water. The organics were collected using a phase separator and concentrated. The crude product was purified by flash column chromatography using EtOAc/hexanes as eluent to yield the title compound as an off white solid (165 mg, 79%). $^1$H NMR (400 MHz, CDCl$_3$) δ 8.54 (s, 1H), 8.12 (m, 2H), 7.79 (m, 2H), 7.48 (m, 2H), 7.38 (m, 2H), 1.54 (s, 9H); $^{19}$F NMR (376 MHz, CDCl$_3$) 5-58.03; ESIMS m/z 421.3 ([M+H]$^+$).

Example 8

Preparation of tert-butyl (4-(1-(4-(pentafluoroethoxy)phenyl)-1H-1,2,4-triazol-3-yl)phenyl)carbamate (Compound 8)

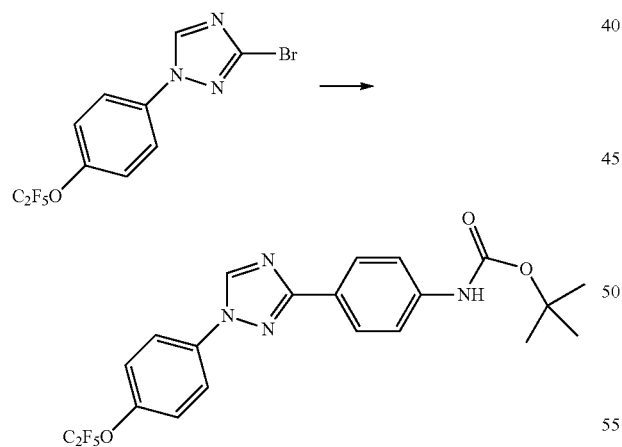

A microwave vial was charged with tert-butyl (4-(4,4,5,5-tetramethyl-1,3,2-dioxaborolan-2-yl)phenyl)carbamate (178 mg, 0.559 mmol), 3-bromo-1-(4-(pentafluoroethoxy)phenyl)-1H-1,2,4-triazole (200 mg, 0.559 mmol), NaHCO$_3$ (94 mg, 1.2 mmol), and Pd(PPh$_3$)$_4$ (39 mg, 0.034 mmol). Dioxane (3.8 mL) and water (1.2 mL) were added, and the capped reaction mixture was heated at 140° C. for 30 min in a Biotage Initiator® microwave reactor with external IR-sensor temperature monitoring from the side of the vessel. The reaction mixture was cooled to RT, and allowed to stand overnight. Water (3 mL) was added to the solution, and a gummy solid formed, which was filtered and air-dried. Recrystallization of this material from MeOH/water gave the title compound as a white solid (180 mg, 66%): $^1$H NMR (400 MHz, CDCl$_3$) δ 8.55 (s, 1H), 8.12 (d, J=8.7 Hz, 2H), 7.80 (d, J=9.0 Hz, 2H), 7.48 (d, J=8.7 Hz, 2H), 7.39 (d, J=8.9 Hz, 2H), 6.61 (s, 1H), 1.54 (s, 9H); $^{19}$F NMR (376 MHz, CDCl$_3$) 5-85.90, -87.86; ESIMS m/z 470 ([M+H]$^+$)

Example 9

Preparation of 4-(1-(4-(perfluoroethoxy)phenyl)-1H-1,2,4-triazol-3-yl)aniline (Compound 9)

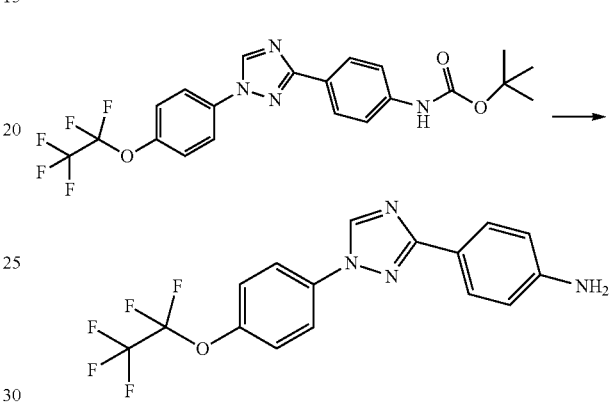

Tert-butyl (4-(1-(4-(perfluoroethoxy)phenyl)-1H-1,2,4-triazol-3-yl)phenyl)carbamate (0.100 g, 0.213 mol) was dissolved in HCl in dioxane (4 N, 3 mL, 12 mmol) and stirred at 40° C. for 1 h. The solution was then cooled, neutralized with saturated aqueous NaHCO$_3$ solution to pH 7, and extracted with diethyl ether (2×10 mL). The combined organic layer was dried and concentrated to afford the title compound as a light tan solid (54 mg, 68%): $^1$H NMR (400 MHz, CDCl$_3$) δ 8.52 (s, 1H), 7.99 (d, J=8.6 Hz, 1H), 7.79 (d, J=9.0 Hz, 1H), 7.37 (d, J=8.8 Hz, 1H), 6.76 (d, J=8.6 Hz, 1H). 3.9 (br s, 2H); ESIMS m/z 371 ([M+H]$^+$).

Example 10

Preparation of 4-(1-(4-(trifluoromethoxy)phenyl)-1H-1,2,4-triazol-3-yl)aniline (Compound 10)

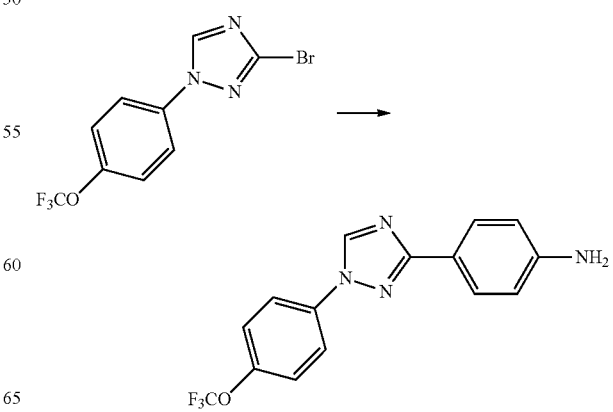

Method A

To a 5-mL microwave vial was added 3-bromo-1-(4-(trifluoromethoxy)phenyl)-1H-1,2,4-triazole (150 mg, 0.487 mmol)), 4-(4,4,5,5-tetramethyl-1,3,2-dioxaborolan-2-yl)aniline (128 mg, 0.584 mmol)], KF (73.6 mg, 1.266 mmol)), and $PdCl_2(PPh_3)_2$ (34.2 mg, 0.049 mmol). Subsequently, MeCN (2.092 mL))/water (2.092 mL)) was added. The reaction vial was then capped and heated at 115° C. for 15 min in a Biotage Initiator® microwave reactor with external IR-sensor temperature monitoring from the side of the vessel. The reaction mixture was cooled to RT and diluted with $CH_2Cl_2$ and water. The organics were collected using a phase separator and concentrated. The crude product was purified by reverse phase flash column chromatography (silica, hexanes/EtOAc) to yield the title compound (125 mg, 80%): $^1$H NMR (400 MHz, $CDCl_3$) δ 8.51 (s, 1H), 7.99 (m, 2H), 7.78 (m, 2H), 7.37 (m, 2H), 6.76 (m, 2H), 3.87 (s, 2H); $^{19}$F NMR (376 MHz, $CDCl_3$) δ −58.04; ESIMS m/z 321.1 ([M+H]$^+$).

Method B

A microwave vial was charged with 4-(4,4,5,5-tetramethyl-1,3,2-dioxaborolan-2-yl)aniline (128 mg, 0.584 mmol), 3-bromo-1-(4-(trifluoromethoxy)phenyl)-1H-1,2,4-triazole (150 mg, 0.487 mmol), $Na_2CO_3$ (1 M, 1.948 mL, 1.948 mmol), and $Pd(PPh_3)_4$ (56.3 mg, 0.049 mmol). The reaction vial was capped and evacuated/backfilled with nitrogen gas (3×). DME (2 mL) was added and the reaction mixture was heated at 100° C. for 15 min in a Biotage Initiator® microwave reactor with external IR-sensor temperature monitoring from the side of the vessel. The reaction mixture was cooled to RT, diluted with $CH_2Cl_2$, and water was added. The layers were separated with a phase separator. The organics were concentrated and purified via flash column chromatography to yield the title compound as an off-white solid (111 mg, 71%): $^1$H NMR (400 MHz, $CDCl_3$) δ 8.51 (s, 1H), 7.99 (m, 2H), 7.78 (m, 2H), 7.37 (m, 2H), 6.76 (m, 2H), 3.87 (s, 2H); $^{19}$F NMR (376 MHz, $CDCl_3$) δ −58.03; ESIMS m/z 321.1 ([M+H]$^+$).

Example 11

Preparation of 4-(1-(4-(perfluoroethoxy)phenyl)-1H-1,2,4-triazol-3-yl)aniline (Compound 9)

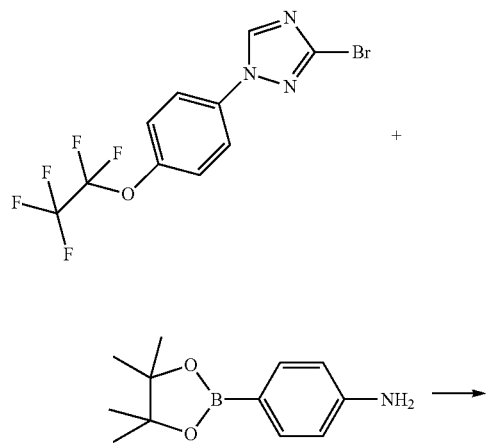

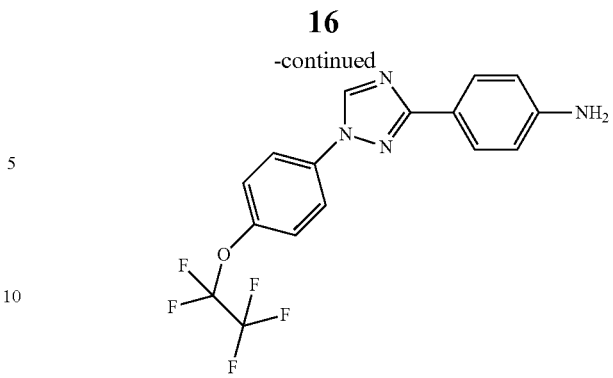

3-Bromo-1-(4-(perfluoroethoxy)phenyl)-1H-1,2,4-triazole (1.5 g, 4.2 mmol) and 4-(4,4,5,5-tetramethyl-1,3,2-dioxaborolan-2-yl)aniline (1.12 g, 5.12 mmol), $Pd(PPh_3)_4$ (0.49 g, 0.424 mmol) and $K_2CO_3$ (1.17 g, 8.52 mmol) were combined in a round bottom flask in 5:1 DME/water (22 mL), and the solution was degassed with nitrogen for 15 min. The reaction was then heated for 18 h at 120° C. The reaction mixture was cooled and diluted with EtOAc and water. The layers were separated and the aqueous layer was extracted with EtOAc (2×50 ml). The combined organic extracts were dried over anhydrous $MgSO_4$ and concentrated onto 8 g of Celite®. The Celite® was loaded onto a silica column and the target molecule was eluted using 0-100% EtOAc/hexanes to afford the title compound as a tan solid (1.13 g, 68%): $^1$H NMR (400 MHz, $CDCl_3$) δ 8.52 (s, 1H), 7.99 (d, J=8.7 Hz, 2H), 7.78 (d, J=9.1 Hz, 2H), 7.36 (d, J=9.1 Hz, 2H), 6.76 (d, J=8.7 Hz, 2H), 3.90 (s, 2H); ESIMS m/z 371.2 ([M+H]$^+$).

We claim:

1. A process comprising:
reacting a compound of formula 1.2 with a ($R_2$—OC(=O)-phenyl)boronic acid, ($R_2$—OC(=O)-phenyl)boronic ester, or potassium ($R_2$—OC(=O)-phenyl trifluoroborate salt, to produce a compound of formula 1.3

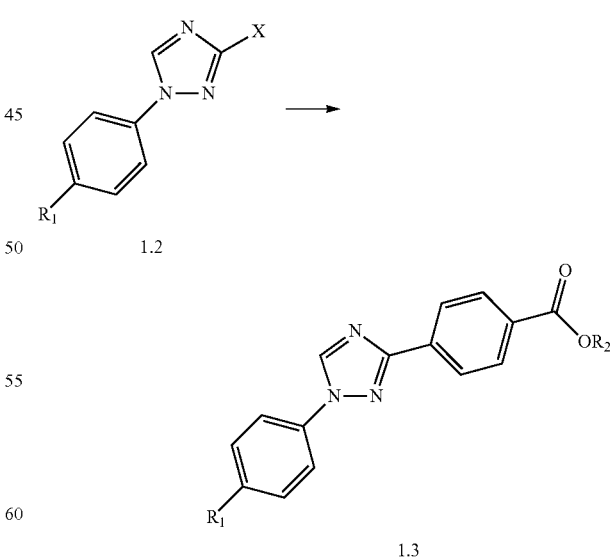

wherein
X is Cl, Br, or I,
$R_1$ is a ($C_1$-$C_6$) haloalkoxy;
$R_2$ is H or ($C_1$-$C_6$) alkyl; and said reacting is conducted in the presence of a base, a palladium catalyst, a polar aprotic solvent.

2. A process according to claim 1 wherein said base is potassium carbonate, sodium carbonate, sodium bicarbonate, potassium fluoride, or mixtures thereof.

3. A process according to claim 1 wherein said palladium catalyst is selected from bis(triphenylphosphine)palladium (II) chloride, tetrakis(triphenylphosphine)palladium (0), or mixtures thereof.

4. A process according to claim 1 wherein $R_1$ is trifluoromethoxy or pentafluoroethoxy.

5. A process according to claim 1 wherein $R_2$ is methyl or ethyl.

6. A process according to claim 1 wherein said solvent is acetonitrile, dioxane, dimethyoxyethane, tetrahydrofuran, or mixtures thereof.

7. A process according to claim 1 further comprising saponifying a compound of formula 1.3 to produce a compound of formula 1.4

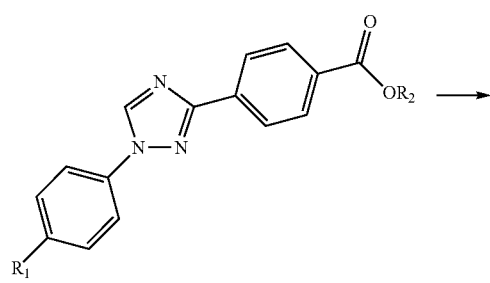

1.3

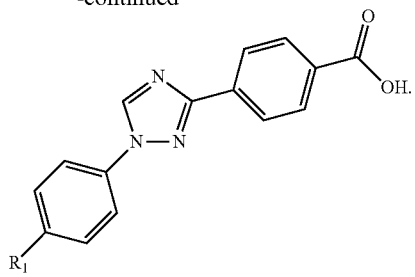

1.4 wherein $R_2$ is $(C_1-C_6)$ alkyl.

8. A compound having the following structure

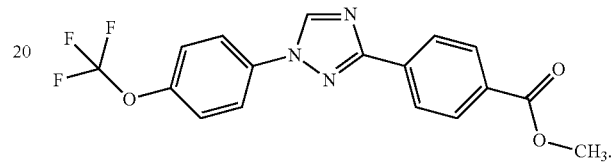

methyl 4-(1-(4-(trifluoromethoxy)phenyl)-1H-1,2,4-triazol-3-yl)benzoate

9. A compound having the following structure

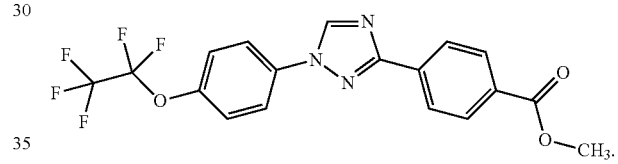

methyl 4-(1-(4-(perfluoroethoxy)phenyl)-1H-1,2,4-triazol-3-yl)benzoate

* * * * *